United States Patent [19]
Binger

[11] Patent Number: 5,723,714
[45] Date of Patent: Mar. 3, 1998

[54] PROCESS FOR THE PREPARATION OF METHYLENECYCLOPROPANE

[75] Inventor: Paul Binger, Mülheim an der Ruhr, Germany

[73] Assignee: Studiengesellschaft Kohle mbH, Mulheim an der Ruhr, Germany

[21] Appl. No.: 513,840
[22] PCT Filed: Sep. 28, 1994
[86] PCT No.: PCT/EP94/03231
  § 371 Date: Sep. 5, 1995
  § 102(e) Date: Sep. 5, 1995
[87] PCT Pub. No.: WO95/09826
  PCT Pub. Date: Apr. 13, 1995

[30] Foreign Application Priority Data
Oct. 1, 1993 [DE] Germany ............... 43 33 491.1

[51] Int. Cl.$^6$ .................................................. C07C 1/32
[52] U.S. Cl. .................... 585/638; 585/639; 585/641
[58] Field of Search ............................ 585/638, 639, 585/641

Primary Examiner—Elizabeth D. Wood
Attorney, Agent, or Firm—Sprung Kramer Schaefer & Briscoe

[57] ABSTRACT

A novel process for the production of methylenecyclopropane from 3-halogen-2-methyl-1-propene (β-methallyl halogenide) by reacting β-methyallyl halogenides with an alkali metal-bis-(trialkylsilyl)-amide, optionally in the presence of an alkali metal alcoholate and/or a corresponding alcohol. Methylenecyclopropane is obtained in a high yield, combined with a low or negligible amount of 1-methylcyclopropene.

13 Claims, No Drawings

PROCESS FOR THE PREPARATION OF METHYLENECYCLOPROPANE

CROSS-REFERENCES TO RELATED APPLICATIONS

This application has been filed under 35 U.S.C. 371 from International Application No. PCT/EP94/03231, which was filed on Sep. 28, 1994, and published as WO 95/09826, on Apr. 13, 1995.

BACKGROUND OF THE INVENTION

1. Field of the Invention

The object of the invention is a novel process for the production of methylenecyclopropane from 3-halogen-2-methyl-1-propene (β-methallyl halogenide).

2. Description of Related Art

Methylenecyclopropane is a highly reactive reagent which can be used in many cases in the organic synthesis. For instance, cyclopropylamines can be produced thereof, which reinforce as special substituent the activity of different pharmaceuticals. The (3+2) cycloadditions with alkenes, catalyzed by transition metals, are resulting in methylenecyclopentane derivatives, which can be used on their part by appropriate substitution as starting materials for the synthesis of natural products (P. Binger, H. M. Büch, Top. Cur. Chem. 1987, 135, 77; B. M. Trost Angew. Chem. 1986, 98, 1; B. M. Trost, Sciences 1991, 1471).

A variety of processes for the production of methylenecyclopropane are already known from the state of the art. Among the variety of methods for the production of methylenecyclopropane (P. Binger, H. M. Büch, Top. Cur. Chem. 1987, 135, 79–151; T. Tsuji, S. Nishida in Patai (Ed. Z. Rappoport) The Chemistry of Cyclopropylgroup; John Wiley, New York 1987, p. 315) the reaction of β-methallylchloride with sodium and potassiumamide reaction of β-methallylchloride with sodium and potassiumamide is outstanding due to its simplicity. This method, originally developed for the preparation of 1-methylcyclopropene (F. Fischer, D. E. Applequist, J. Org. Chem. 1965, 30, 2089) can be used for the preparation of methylenecyclopropane, if higher boiling ethers (dioxane, di-butylether) are used instead of THF as solvents at their boiling points. By using sodium amide, a mixture of methylenecyclopropane and 1-methylcyclopropene is then obtained from β-methallylchloride in a ratio of 4:1 and in a yield of maximally 75%, which will be transferred in a second reaction step by means of potassium tert.-butylate in DMSO into methylenecyclopropane in a yield of 98%. (Total yield of methylenecyclopropane is 70% (R. Köster, S. Arora, P. Binger, Synthesis, 6, 1971, 322–323; R. Köster, S. Arora, P. Binger, Liebigs Ann. Chem. 1973, 1219–1235). The use of potassium amide has the advantage, that the methylenecyclopropane can be obtained directly in a purity of 94–97%, however, the yield is then decreasing to 36% in boiling THF (R. Köster, S. Arora, P. Binger, Angew. Chem. 1969, 81, 186), to 61% in boiling di-butylether (R. K öster, S. Arora, P. Binger, Liebigs ann. Chem. 1973, 1219–1235).

Pure methylenecyclopropane can also be obtained in boiling THF with a mixture of the bases sodium amide/sodium-tert.-butylate in a ratio of 3:1 in a yield of 43%, however, this mixture of bases has to be employed in an excess of 4.5 (P. Caubere, G. Coudet, Bull. Soc. Chem. FR. 1971, 2234; J. R. Salaun, J. Champion, J. M. Conia, Org. Synth. 57, 1977, 36–40).

The disadvantage of all these process variations is, that one has to work in a heterogeneous system, since sodium amide and potassium amide are not soluble in the afore mentioned solvents. This excludes a production of methylenecyclopropane in an industrial scale, because working with solid sodium amide and potassium amide, respectively, is not acceptable for security reasons.

Therefore, the aim of the invention is an improved process for the production of methylenecyclopropane in an industrial scale, which overcomes the afore mentioned disadvantages of the state of the art.

SUMMARY OF THE INVENTION

It has been found now, that methylenecyclopropane can be prepared also in an industrial scale from β-methallylchloride in solution, and therefore without danger, by using alkali metal-bis-(trialkylsilyl)-amides as bases, particularly those with sodium or potassium as alkali metals. A further advantage of this novel method is, that high yields of methylenecyclopropane (up to 89% relative to 70%) can be obtained.

The afore mentioned problem is solved by a process for the production of methylenecyclopropane from 3-halogen-2-methyl-1-propene (β-methylallylhalogenide), characterized by reacting the β-methylallylhalogenide with an alkali metal-bis-(trial-kylsilyl)-amide of the general formula (I)

$$\text{Me—N (SiR}_3)_2 \quad \text{(I)}$$

wherein

Me represents an alkali metal cation selected from lithium, sodium or potassium, and R represents a short-chain, straight-chain or branched, saturated alkyl group having 1 to 4 C-atoms, optionally in presence of an alkali metal alcoholate or a corresponding alcohol of the general formula (II)

$$\text{MeOR or HOR} \quad \text{(II)}$$

wherein

Me and R have the above mentioned meaning, in a high-boiling organic solvent at a temperature above room temperature.

DESCRIPTION OF THE PREFERRED EMBODIMENTS

Due to the fact, that the reaction primarily forms the thermally instable 1-methylcyclopropene (3), which is, depending on the selected base, rearranged during the reaction in a high degree up to completely into the methylenecyclopropane (2), it is recommended to work in boiling solvents, in order to eliminate as soon as possible the product mixture of methylenecyclopropane (2) [boiling point: 12° C.] and 1-methylcyclopropene (3) [boiling point: 8° C.] from the hot reaction medium. The mixture of methylenecyclopropane (2) and 1-methylcyclopropene (3) or, optionally pure methylenecyclopropane (2), will then be trapped in a cold trap at −30° to −78° C., and will be received by appropriate choice of the reflux condenser without impurities. Optionally, the rearrangement of the by-product of 1-methylcyclopropene (3) into methylenecyclopropane (2) succeeds in a second reactions step by simply passing a mixture of methylenecyclopropane (2), 1-methylcyclopropene (3) through a solution of potassium-tert.-butylate in DMSO, almost without loss.

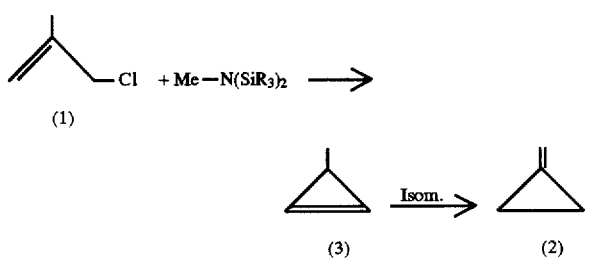

Though principally all imaginable 3-halogen-2-methyl-1-propenes (β-methallylhalogenide) can be used, 3-chlor-2-methyl-1-propene (β-methallylchloride) is particularly preferred according to the present invention, since this compound is a commercial product, which is available without any problem on the chemical market.

The same is valid for the alkali metal-bis-(trialkylsilyl)-amides of the general formula (I). Though generally the alkyl group can be represented by a short-chain, straight-chain or branched, saturated alkyl group having 1 to 4 C-atoms, it is preferred according to the present invention, to use the trimethylsilylamides of the alkali metals, because they can be produced in a particularly simple way, respectively, they are also available as commercial products.

The best yields of unsaturated three membered rings are obtained by using sodium-bis-(trimethylsilyl)amide. They are in the range of between 79% and 90% when working in solvents, which are boiling above 100° C. (toluene, o-xylene, di-n-butyl-ether). However, there always will be obtained a mixture of the unsaturated hydrocarbons methylenecyclopropane and 1-methylcyclopropene, such that a subsequent isomerization of 1-methylcyclopropene into methylenecyclopropane will be necessary. Generally the ratio of methylenecyclopropane to 1-methylcyclopropene is from 77–86:23–14. The subsequent isomerization of 1-methylcyclopropene into methylenecyclopropane is no more necessary when alkali metal alcoholates are added to the sodium-bis-(trimethylsilyl)amide, e.g. potassium-tert.-butanolate. By this way methylenecyclopropane can be obtained in a yield of 85% and having a purity of 97%. Therefore, the additional use of the alkali metal alcoholates, particularly potassium-tert.-butanolate, is preferred.

By using potassium-bis-(trimethylsilyl)amide in high-boiling solvents, methylenecyclopropane could be directly obtained in a high-purity grade (96–100%).

When using lithium-bis-(trimethylsilyl)amide, the reaction succeeded by addition of an equimolar amount of potassium-tert.-butanolate. By this way, a mixture of methylenecyclopropane and 1-methylcyclopropene in a ratio of 88:12 was obtained from β-methallylchloride, lithium-bis-(trimethylsilyl)-amide and potassium-tert.-butanolate in a ratio of 1 to 1–1.3 in boiling toluene in a yield of 80%. β-methallylchloride, lithium-bis-(trimethylsilyl)-amide and potassium-tert.-butanolate, in a mole ratio of 1 to 0.2 to 1.2 resulted in 98% of methylenecyclopropane, yield: 17% (relative to charged lithiumamide 86%, respectively).

Other alkali metal amides than trialkylsilylamides, as e.g. lithium-, sodium- or potassium-diethylamide or -diisopropyl-amide do not react with β-methallylchloride to the unsaturated three membered ring compounds methylenecyclopropane and 1-methylcyclopropene.

A particularly preferred embodiment of the present invention is therefore characterized by using as alkali metal-bis-(tri-alkylsilyl)-amide of the general formula (I):

a) potassium-bis-(trimethylsilyl)-amide alone
b) sodium-bis-(trimethylsilyl)-amide alone or in a mixture with an alkali metal alcoholate and/or a corresponding alcohol of the general formula (II) or
c) lithium-bis-(trimethylsilyl)-amide in a mixture with an alkali metal alcoholate.

In the same way it is of course possible, to use mixtures of alkali metal-bis-(trialkylsilyl)-amides.

The mole ratios of the reactants involved in the reaction, can be adjusted in a different way to optimize the yield and/or the purity. It is particularly preferred, to adjust the mole ratio of 3-halogen-2-methyl-1-propene to the alkali metal-bis-(trialkylsilyl)-amides in the range of 1–1.4 to 1, particularly in the range close to 1 to 1, since in between this range particularly high yields and high grades of purity of the desired compound will be obtained.

Though in the case of using alkali metal alcoholates or corresponding alcohols, which are not participating directly in the reaction, it is however preferred, to adjust the mole ratio of metal-bis-(trialkylsilyl)-amides to alkali metal alcoholates or corresponding alcohols in a defined manner. Particularly preferred is a mole ratio of metal-bis-(trialkylsilyl)-amides to alkali metal alcoholates or corresponding alcohols in a range of 0.6:1 to 1.5:1, particularly to 1:1.2.

It is principally possible, to carry out the process according to the invention in a number of high-boiling organic solvents. Particularly preferred organic solvents have boiling points above 100° C. Therefore, the organic solvent is preferably selected from aromatic hydrocarbons, particularly toluene or xylene, aliphatic ethers, particularly tetrahydrofuran, dioxane and di-n-butylether, and polyethylene glycol-dialkyl-ethers, particularly monoglyme and diglyme. In the same way also mixtures of solvents are applicable besides the pure solvents.

By carrying out the reaction according to the invention, it is preferred to adjust the reaction temperature in a range of from 60° and 150° C., and particularly from 110° to 150° C. Thereby, the high-volatile cyclo compounds are readily eliminated from the reaction system. Particularly high yields are obtained by using high-boiling solvents.

Therefore, it is possible with the aid of the present invention, to provide methylenecyclopropane as a highly reactive reagent in the organic synthesis in an industrial scale, such that it is possible with the aid of the present invention to apply methylenecyclopropane for the preparation of cyclopropylmethylamines, which can be used as substituents in various pharmaceuticals. Furthermore, the methylenecyclopropane, now available in an industrial scale, is suited for the application in 3+2 cycloadditions with alkenes for the preparation of methylenecyclopentane derivatives.

EXAMPLES

EXAMPLE 1

In a 2 l four-neck flask provided with a 250 ml dropping funnel, reflux condenser, KPG-stirrer and inert gas inlet, 500 g (2.73 mole) of sodium-bis-(trimethylsilyl)-amide were dissolved in 700 ml of toluene under protective gas (argon) and heated to boil. At this temperature, 199 g (2.2 mole) of β-methallylchloride was added dropwise under stirring within 4 hours. Immediately, the mixture of methylenecyclopropane and 1-methyl-cyclopropene escaped via the reflux condenser in form of a continuous gas stream, which was trapped in a cold trap at −78° C. After the reaction being completed, 103 g (1.9 mole, 86%) of a liquid which is colourless at −78° C., was found in the cold trap, the gaschromatic analysis (GC) thereof, showed, that it consisted of 77% methylenecyclopropane and 23% of 1-methylcyclopropene. Filtration or decantation or distillation, respectively, of the reaction mixture at 20° C./0.05 bar yields 921 g of a colourless distillate, that almost quantitatively contained the released hexamethyl-disilazane (GC: 60.8% of toluene; 38.5% of hexamethyl-disilazane). The residue consisted of 274 g of a colourless powder. The distillate could be used directly for the preparation of the sodium-bis-(trimethylsilyl)-amide.

EXAMPLE 2

Analogous to example 1, 10.7 g (79%) of methylenecyclopropane and 1-methylcyclopropene in a ratio of 86:14 (GC), and 105 g of a colourless distillate having a boiling point of 20° C./0.05 bar, of the composition (GC) of 36% hexamethyl-disilazane and 63% of di-n-butylether were obtained from 57.2 g (0.31 mole) of sodium-bis-(trimethylsilyl)-amide and 22.6 g (0.25 mole) of β-methallylchloride in 100 ml of boiling di-n-butylether.

EXAMPLE 3

Analogous to the method described in example 2, 9.2 g (85%) of methylenecyclopropane and 1-methylcyclopropene in a ratio of 97:3 and 102 g of a colourless distillate having a boiling point of 20° C./0.05 bar, of the composition (GC) of 33% hexamethyl-disilazane and 66.4% of di-n-butylether were obtained from 48 g (0.26 mole) of sodium-bis-(trimethylsilyl)-amide, 22.6 g (0.20 mole) potassium-tert.-butanolate and 18.1 g (0.20 mole) of β-methallylchloride.

EXAMPLE 4

61.4 g (0.31 mole) of potassium-bis-(trimethylsilyl)-amide were dissolved in 100 ml of o-xylene, and 22.6 g (0.25 mole) of β-methallylchloride was added dropwise at 145° C. (reflux under stirring) during 1 h. The released gas was trapped at −78° C. in a cold trap. 9.2 g (68%) of 97% methylene-cyclo-propane was obtained, which was contaminated with 3% of 1-methylcyclopropene (GC). Distillation of the reaction mixture yield 129 g of a colourless distillate having a boiling point of up to 30° C./0.05 bar and having a composition (GC) of 26% of hexamethyl-disilazane and 70% of o-xylene; the balance (4%) consisted of 5 unknown compounds.

EXAMPLE 5

58.3 g (0.35 mole) of lithium-bis-(trimethylsilyl)-amide and 51.0 g (0.46 mole) of potassium-tert.-butanolate were dissolved in 150 ml of toluene (heat-evolution up to about 40° C.), and heated (reflux) up to 110° C. 31.6 g (0.35 mole) of β-methallylchloride was added dropwise under stirring within about 1 hour, whereby altogether 15.2 g (80%) of a mixture of 88% methylenecyclopropane and 12% of 1-methyl-cyclopropene (GC) escaped, which was collected in a cold trap at −78° C. as a colourless liquid. From the remaining reaction mixture it was obtained by distillation up to 20° C./0.1 bar, 190 g of a colourless liquid having a composition (GC) of 30% of hexamethyl-disilazane and 70% of toluene. The residue consisted of 62 g of a colourless solid.

I claim:

1. Process for the preparation of methylenecyclopropane from 3-halogen-2-methyl-1-propene (β-methallyl halogenide), comprising reacting the β-methallyhalogenide with an alkali metal-bis-(trialkylsilyl)-amide of the general formula (I)

Me—N(SiR$_3$)$_2$     (I)

wherein

Me represents an alkali metal cation selected from lithium, sodium or potassium, and R represents a short-chain, straight-chain or branched, saturated alkyl group having 1 to 4 C-atoms, optionally in presence of an alkali metal alcoholate or a corresponding alcohol of the general formula (II)

MeOR or HOR     (II)

wherein

Me and R have the above mentioned meaning, in an organic solvent having a boiling point above 100° C. at a temperature above room temperature.

2. Process according to claim 1, wherein the 3-halogen-2-methyl-1-propene is 3-chlor-2-methyl-1-propene (β-methallyl chloride).

3. Process according to claim 1, wherein R is a methyl group in the general formula (I).

4. Process according to claim 1, comprising using as the alkali metal-bis-(trialkylsilyl)-amide of the general formula (I):

a) potassium-bis-(trimethylsilyl)-amide alone b) sodium-bis-(trimethylsilyl)-amide alone or in a mixture with an alkali metal alcoholate and/or a corresponding alcohol of the general formula (II) or c) lithium-bis-(trimethylsilyl)-amide in a mixture with an alkali metal alcoholate.

5. Process according to claim 1, comprising using potassium-tert.-butanolate as the alkali metal alcoholate of the general formula (II).

6. Process according to claim 1, wherein the organic solvent is selected from the group consisting of aromatic hydrocarbons, aliphatic ethers, and polyethylene glycol-dialkylethers.

7. Process according to claim 6, wherein the organic solvent is selected from the group consisting of toluene, xylene, tetrahydrofuran, monoglyme and diglyme.

8. Process according to claim 1, wherein the reaction temperature is in a range of from 60° to 150° C.

9. Process according to claim 8, wherein the reaction temperature is in a range of from 110° to 150° C.

10. Process according to one or more of the claim 1 wherein the mole ratio of 3-halogen-2-methyl-1-propene to alkali metal-bis-(trialkylsilyl)-amide of the general formula (I) is in a range of 1–1.4 to 1.

11. Process according to claim 10, wherein the mole ratio of 3-halogen-2-methyl-1-propene to alkali metal-bis-(trialkylsilyl)-amide of the general formula (I) is 1:1.

12. Process according to claim 1, wherein the mole ratio of alkali metal-bis-(trialkylsilyl)-amide of the general formula (I) to alkali metal alcoholate of the general formula (II) or the corresponding alcohol is in a range of from 0.6:1 to 1.5:1.

13. Process according to claim 12, wherein the mole ratio of alkali metal-bis-(trialkylsilyl)-amide of the general formula I to alkali metal alcoholate of the general formula (II) or the corresponding alcohol is 1:1.

* * * * *